United States Patent
Colby et al.

(10) Patent No.: US 9,533,935 B2
(45) Date of Patent: Jan. 3, 2017

(54) METHODS OF DIRECT ADDITION OF (METH) ACRYLIC ACID TO BIO-BASED OILS

(71) Applicant: 3M INNOVATIVE PROPERTIES COMPANY, St. Paul, MN (US)

(72) Inventors: Joshua L. Colby, Lino Lakes, MN (US); Lianzhou Chen, Woodbury, MN (US); Kwame Owusu-Adom, Stone Mountain, GA (US); Aaron E. Hutt, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/778,644

(22) PCT Filed: May 1, 2014

(86) PCT No.: PCT/US2014/036292
§ 371 (c)(1),
(2) Date: Sep. 21, 2015

(87) PCT Pub. No.: WO2014/186137
PCT Pub. Date: Nov. 20, 2014

(65) Prior Publication Data
US 2016/0053200 A1    Feb. 25, 2016

Related U.S. Application Data

(60) Provisional application No. 61/824,618, filed on May 17, 2013.

(51) Int. Cl.
| | | |
|---|---|---|
| C07C 67/04 | (2006.01) |
| C07C 69/54 | (2006.01) |
| C07C 67/31 | (2006.01) |
| C11C 3/00 | (2006.01) |

(52) U.S. Cl.
CPC .............. *C07C 67/04* (2013.01); *C07C 67/31* (2013.01); *C07C 69/54* (2013.01); *C11C 3/00* (2013.01)

(58) Field of Classification Search
CPC .............. C07C 67/04; C07C 69/73; C11C 3/00
See application file for complete search history.

(56) References Cited

U.S. PATENT DOCUMENTS

| | | |
|---|---|---|
| 4,225,498 A | 9/1980 | Baudouin |
| 2005/0203246 A1 | 9/2005 | Thames |

OTHER PUBLICATIONS

Eren, T. et al., Synthesis and polymerizatin of the bromoacrylated plant oil triglycerides to rigid, flame-retardant polymers, 2004, Journal of Applied Polymer Science, vol. 91, pp. 2700-2710.*
Pelletier, H., et al., Preparatinof acrylated and urethanated triacylglycerols, 2006, European Journal Lipid Sci. Technol., vol. 108, pp. 411-420.*
Montero de Espinosa, L., et al., A new route to acrylate oils: crosslinking and properties of Acrylate Triglycerides form high oleic sunflower oil, 2009, Journal of Polymer Science: Part A: Polymer Chemistry, vol. 47, pp. 1159-1167.*
ASTM D6866-12, Standard Test Methods for Determining the Biobased Content of Solid, Liquid, and Gaseous Samples Using Radiocarbon Analysis, 14 pgs.
Wang, "Sulfamic acid as green, efficient, recyclable and reusable catalyst for direct addition of aliphaticacid with cyclic olefins", Catalysis Letters, Jul. 2004, vol. 96, No. 1-2, pp. 71-74, XP002462263.
Zhang, "One-step acrylation of soybean oil (SO) for the preparation of SO-based macromonomers," Green Chemistry, 2013, vol. 15, No. 3, pp. 641-645, XP002729111.
International Search report for PCT International Application No. PCT/US2014/036292 mailed on Sep. 12, 2014, 3 pages.

* cited by examiner

*Primary Examiner* — Yate K Cutliff
(74) *Attorney, Agent, or Firm* — Adrian L. Pishko

(57) ABSTRACT

(Meth)acrylates are prepared in a single-step method from a mixture of (meth)acrylic acid and at least one biobased oil and/or its derivative(s), including at least one unsaturation. The (meth)acrylates are made by directly adding the (meth)acrylic acid to the biobased oil by reacting in the presence of an acid catalyst, including an inorganic or organic acid having at least one oxygen atom present thereon and which possesses at least one acid functionality having an ionization constant in water which is not greater than 3.

20 Claims, No Drawings

METHODS OF DIRECT ADDITION OF (METH) ACRYLIC ACID TO BIO-BASED OILS

CROSS REFERENCE TO RELATED APPLICATIONS

This application is a national stage filing under 35 U.S.C. 371 of PCT/US2014/036292, filed May 1, 2014, which claims priority to U.S. Application No. 61/824618, filed May 17, 2013, the disclosure of which is incorporated by reference in its/their entirety herein.

TECHNICAL FIELD

The present disclosure relates to directly adding (meth) acrylic acid to biobased oils and/or their derivatives.

BACKGROUND (Meth)acrylate functional biobased oils (derived from plants and animals) and biobased oil derivatives are an important platform of chemicals. For example, acrylated epoxidized soybean oil can be a starting material for coatings, adhesives, plasticizers, inks, paints, lubricants and other applications. (Meth)acrylate functional oils are traditionally synthesized through a two step process: 1) epoxidation of unsaturations in the hydrocarbon structure of the oil, followed by 2) (meth)acrylation of the epoxide groups to yield a desired product. Scheme I illustrates such a global reaction scheme using soybean oil and acrylic acid as example starting materials.

Scheme I

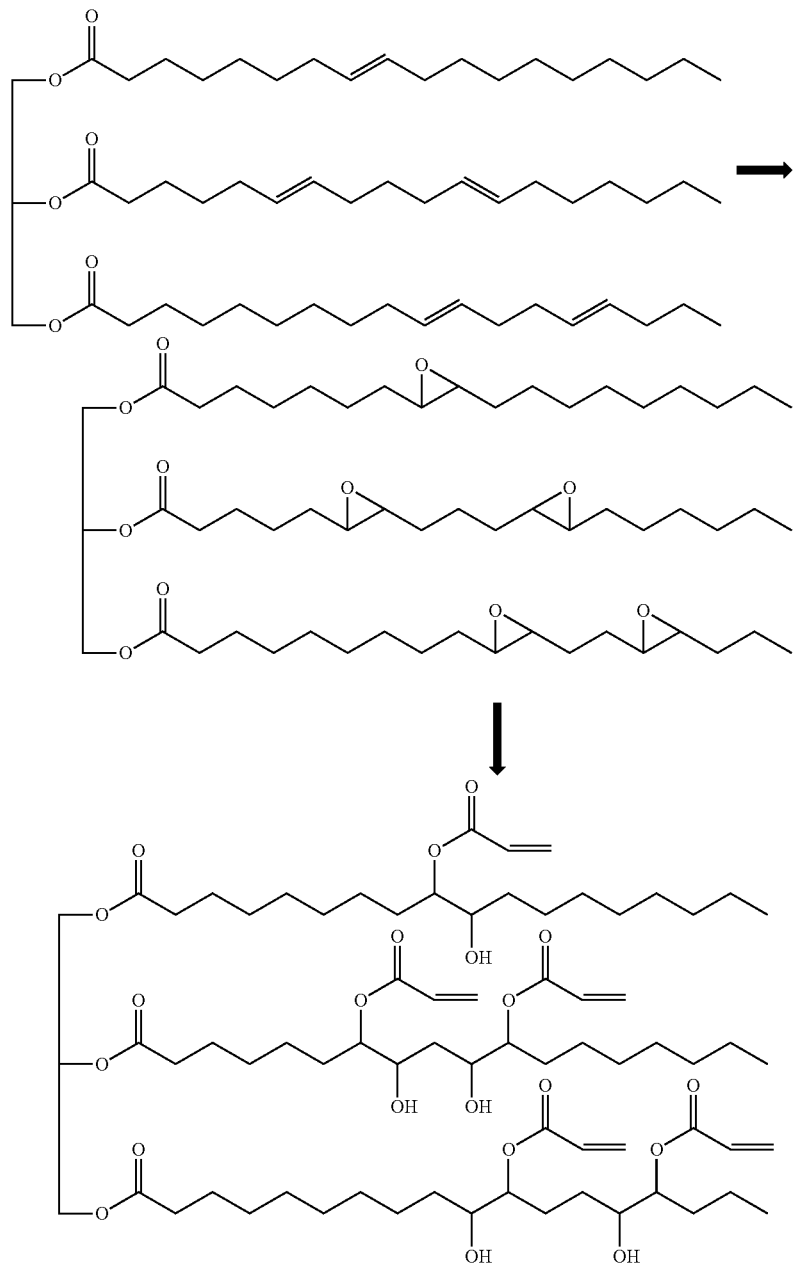

SUMMARY

The present disclosure provides improvements to methods associated with preparing (meth)acrylate functional biobased oils and derivatives thereof.

In a first embodiment, the present disclosure provides a method of making a (meth)acrylate including reacting (meth)acrylic acid with at least one biobased oil, a derivative thereof, or a combination thereof, containing at least one unsaturation, in the presence of an acid catalyst. The acid catalyst includes a strong inorganic or organic acid having at least one oxygen atom present thereon and which possesses at least one acid functionality having an ionization constant in water which is not greater than 3.

Various unexpected results and advantages are obtained in exemplary embodiments of the disclosure. One such advantage of exemplary embodiments of the present disclosure is that direct addition of (meth)acrylic acid to one or more biobased oils and/or their derivatives could reduce material and processing costs associated with manufacturing (meth)acrylate functional oils and (meth)acrylate functional oil derivatives. Another potential advantage of exemplary embodiments of the present disclosure is the ability to prepare (meth)acrylate functional oils and oil derivatives without adding hydroxyl groups at the sites of unsaturation, as occurs during a two-step process involving epoxidation and acrylation. Such hydroxyl groups are illustrated in Scheme I above.

An additional advantage of exemplary embodiments of the present disclosure is that the acid catalyst (e.g., a sulfuric acid catalyst, a sulfonic acid catalyst, or combinations thereof) employed in the single-step acrylation methods disclosed herein lacks certain undesirable characteristics that some catalysts exhibit, for instance $BF_3 \cdot Et_2O$, (Boron trifluoride diethyl etherate), e.g., they are less toxic, plus they produce fewer hazardous byproducts. Further, in embodiments in which the acid catalyst comprises a heterogeneous catalyst, the process does not require catalyst neutralization and/or filtration steps. Moreover, the one-step methods disclosed herein are more easily tunable with respect to the number of unsaturations that are acrylated, as compared to a two-step acrylation method.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION (Meth)acrylic functional biobased oils and biobased oil derivatives have been employed as starting materials for coatings, adhesives, plasticizers, inks, paints, lubricants and other applications. Typically, (meth)acrylic functional biobased oils (and their derivatives) are prepared by a two-step process, and it is beneficial to reduce the time and materials needed to make (meth)acrylic functional biobased oils and derivatives thereof. There is a need for a more efficient and safe process for the direct addition of (meth) acrylic acid to biobased oils and their derivatives.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

As used in this specification and the appended embodiments, the singular forms "a", "an", and "the" include plural referents unless the content clearly dictates otherwise. Thus, for example, reference to "a compound" includes a mixture of two or more compounds. As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "biobased oil" refers to any one or more oils from plant or animal sources, and any fatty acid and/or fatty acid ester derivatives thereof. For convenience, the use of the terms "biobased oil" and "biobased oils" encompasses at least one biobased oil, a derivative thereof, and any combination of at least one biobased oil and fatty acid and/or fatty acid ester derivative thereof.

The term "(co)polymer" is inclusive of both homopolymers containing a single monomer and copolymers containing two or more different monomers.

The term "(meth)acrylic" or "(meth)acrylate" is inclusive of both acrylic and methacrylic (or acrylate and methacrylate).

The term "aliphatic group" means a saturated or unsaturated linear or branched hydrocarbon group. This term is used to encompass alkyl, alkenyl, and alkynyl groups, for example.

The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkylene group" refers to a divalent alkyl group.

The term "heteroalkyl group" means an alkyl group having at least one —$CH_2$— replaced with a heteroatom such as O or S. In many embodiments, the heteroalkyl group is a monovalent polyether group. The term "heteroalkylene group" refers to a divalent heteroalkyl group. In many embodiments, the heteroalkylene group is a divalent polyether group.

The term "alicyclic group" means a cyclic hydrocarbon group having properties resembling those of aliphatic groups. The term "aromatic group" or "aryl group" means a mono- or polynuclear aromatic hydrocarbon group. The term "unsaturation" means either a double bond between two atoms (e.g., C═C), or a triple bond between two atoms (e.g., C≡C).

When a group is present more than once in a formula described herein, each group is "independently" selected, whether specifically stated or not. For example, when more than one R group is present in a formula, each R group is independently selected.

The term "component" refers to any compound (e.g., any reactant), heterogeneous catalyst, solvent, or other material, which is present in a reactor.

The term "continuous" process refers to a process with non-interrupted flow or semi-non-interrupted flow (i.e., pulsed flow) of material(s) in and out of the reactor once the system is operating at steady state. Preferably, a "continuous reactor" refers to a fixed-bed reactor comprising a heterogeneous catalyst with a non-interrupted flow of reactants. In a continuous process of this disclosure, a reactor, typically a tubular reactor, having an inlet for reactants and an outlet for products is charged with a fixed bed of solid acid catalyst and used to perform the desired chemical transformation(s). This reactor configuration, often described as a "packed-bed reactor," can be advantageous when compared to homogeneously catalyzed batch reactions for a number of reasons including: ease of reaction; tighter control over process variables (e.g., temperature, pressure and residence time); higher catalyst to reactant ratio (facilitating higher rates of reaction); and elimination of a catalyst filtration and/or neutralization step. As an alternative to using a packed-bed reactor configuration, other well known continuous reactor configurations may be employed such as "continuous stirred tank" reactors.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Thus, in one exemplary embodiment, the disclosure provides a method of making a (meth)acrylate comprising reacting (meth)acrylic acid with at least one biobased oil (i.e., a biobased oil, a derivative thereof, or a combination thereof) including at least one unsaturation. The reacting occurs in the presence of an acid catalyst comprising an inorganic or organic acid having at least one oxygen atom present thereon and which possesses at least one acid functionality having an ionization constant in water which is not greater than 3. Some suitable acid catalysts include, for example, a sulfuric acid catalyst, a sulfonic acid catalyst, or a combination thereof.

A single-step acrylation of soybean oil has been reported by Zhang et al. (*Green Chem.*, 2013, vol. 15, pp. 641-645). In particular, Zhang et al. disclose a one-step method for preparing acrylated soybean oil "by reacting soybean oil (SO) and acrylic acid (AA) directly under the catalysis of $BF_3.Et_2O$." (Abstract of Zhang et al.) Zhang et al. disclose the use of only the one catalyst, boron trifluoride etherate (i.e., $BF_3.Et_2O$). Moreover, Zhang et al. refer to the preparation of oleic estolides with protonic acids, disclosing that "[b]ecause the protonic acids contained certainly some water which would prevent the formation of ester linkages, vacuum was applied during the reactions to remove water. Therefore, protonic acids are not suitable for catalyzing the addition of AA because the required vacuum will also remove AA." (Page 641 of Zhang et al.) There would not be any reason to react (meth)acrylic acid with a biobased oil in the presence of an acid catalyst comprising a sulfuric acid and/or a sulfonic acid, for example, at least because both sulfuric acid and sulfonic acid are protonic acids.

In certain embodiments, the acid catalyst comprises a homogeneous catalyst, while in alternate embodiments the acid catalyst comprises a heterogeneous catalyst, such as a cation exchange resin. The structure of the acid catalyst is not particularly limited and includes a strong acid functional group. In particular, the acid catalyst comprises a strong inorganic or organic acid having at least one oxygen atom present thereon and which possesses at least one acid functionality having an ionization constant in water which is not greater than 3, or not greater than 2, or not greater than 1. For example and without limitation, the acid catalyst preferably comprises a sulfuric acid functional group, a sulfonic acid functional group, or a combination thereof. In certain exemplary embodiments, the sulfuric acid functional group and/or sulfonic acid functional group is bound to a $C_1$-$C_{30}$ aliphatic group, aromatic group, or heteroalkyl group, a polymer or (co)polymer, or an inorganic group. The acid catalyst has sufficient strength to catalyze the reaction between the (meth)acrylic acid and the at least one biobased oil.

Suitable homogeneous acid catalysts include for example and without limitation, sulfuric acid, methanesulfonic acid, p-toluenesufonic acid, fluorosulfuric acid, and trifluoromethanesulfonic acid. Suitable heterogeneous acid catalysts include for example and without limitation, a sulfonated styrene divinylbenzene copolymer, a fluorosulfonic acid polymer on amorphous silica support, and combinations thereof.

Suitable cation exchange resins include those commercially available from Dow Chemical Company (Midland, Mich.) under the trade name AMBERLYST. In certain embodiments, AMBERLYST 36D is a particularly preferred heterogeneous acid catalyst. In some embodiments the acid catalyst comprises a material such as a polymer, zeolite, or other solid structural material having acidic functional groups affixed thereto. Suitable acid catalysts comprise acidic functional groups, such as comprising sulfonic acid and/or sulfuric acid. A wide variety of commercially available solid (typically, resin) acid catalysts may be used with a packed bed reactor, for example, in a continuous process. In particular, solid acid (heterogeneous) catalysts may be advantageously used in performing the desired chemical transformation(s) disclosed herein including, but not limited to, sulfonated styrene divinylbenzene copolymers (e.g., those available under the trade name AMBERLYST, for instance AMBERLYST 36D or AMBERLYST 70) and high fluorine content aliphatic sulfonic acids (e.g., those available under the trade name NAFION). Another suitable heterogeneous acid catalyst is commercially available from Sigma-Aldrich (St. Louis, Mo.) under the trade name SAC-13. SAC-13 is a fluorosulfonic acid polymer on amorphous silica support.

Selection of a suitable solid acid catalyst material is typically determined by cost, rate of reaction, and selectivity to desired products. One particular type of resin, macroreticular resin, is particularly preferred because it is inexpensive and available in a wide variety of different physical and/or chemical structures. Varying catalyst features such as catalyst surface area, porosity, and acidity can be tuned by varying resin properties such as the extent of crosslinking and degree of sulfonization, facilitating the selection of a suitable catalyst for each desired reaction. Selection of such features is within the skill of one skilled in the art.

Preferably, a suitable acid catalyst comprises an anhydrous acid catalyst, which is typically commercially available. Additionally, conventional methods for preparing anhydrous acid catalysts are also optionally employed. For example, one method to prepare an anhydrous homogeneous acid catalyst includes dissolving the catalyst material in an organic solvent, and then subjection to elevated temperature and rotary evaporation to remove water from the homogeneous catalyst. For example, to prepare an anhydrous heterogeneous acid catalyst, the catalyst material is preferably dried in an oven at elevated temperature to remove water from the heterogeneous catalyst.

In certain embodiments of methods according to the present application, the reacting of (meth)acrylic acid with a biobased oil includes water present in an amount of no more than 20% by weight of all of the components present in the reactor. For example, in certain embodiments the reacting of (meth)acrylic acid with a biobased oil occurs in the presence of water in an amount between 0% and 20% by weight of the total components present, or between 0% and 15%, or between 0% and 10%, or between 0% and 5%, or between 0% and 2%, or between 0.1% and 5%, or between 0.5% and 5% by weight of the total components present in the reactor.

In certain embodiments, the (meth)acrylic acid comprises acrylic acid or methacrylic acid, while in other embodiments the (meth)acrylic acid comprises a combination of acrylic acid and methacrylic acid.

By heating one or a mixture of more than one biobased oil with (meth)acrylic acid in the presence of a sufficiently strong acid catalyst, the (meth)acrylic acid can be directly added to the biobased oil through a reaction with a double bond, typically a carbon-carbon double bond. Scheme II below illustrates such a global reaction scheme using soybean oil and acrylic acid as example starting materials. It should be understood that Scheme II provides just one sample result structure of many possibilities, due to the variety of potential locations of acrylation. It has been discovered that the reaction tends to be equilibrium limited, with higher concentrations of (meth)acrylic acid and lower temperatures favoring higher conversions of unsaturations to acrylates. In contrast, stronger acid catalysts, higher temperatures favor higher rates of reaction.

Scheme II

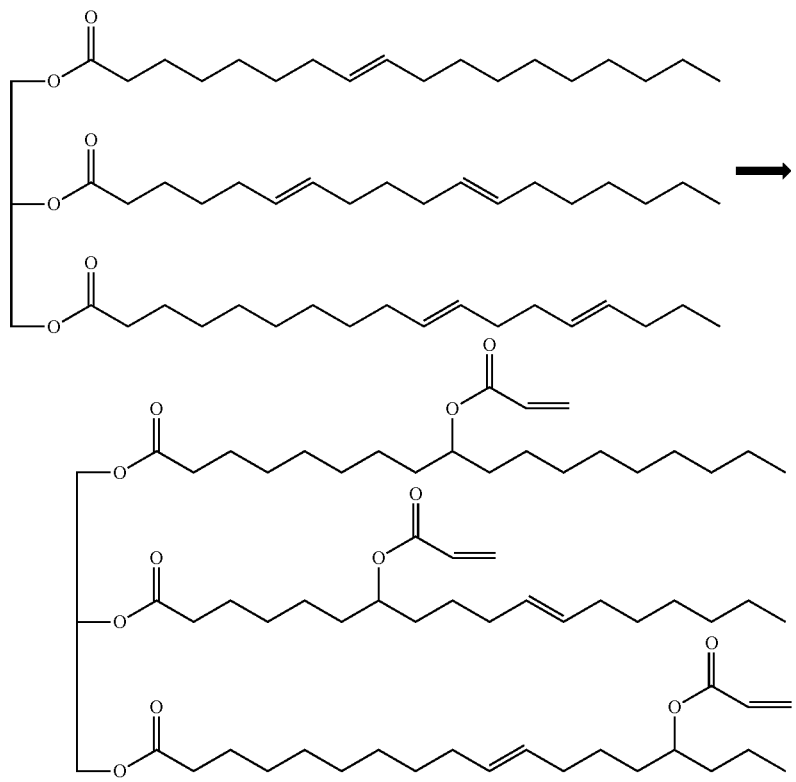

The specific one or more biobased oils are not particularly limited, with the proviso that at least one unsaturation is present per biobased oil molecule. Preferably, each biobased oil molecule comprises as least two unsaturations, or at least three unsaturations, or at least four unsaturations, or even more than four unsaturations. The at least one biobased oil is obtained from a plant or animal. For example and without limitation, the at least one biobased oil is preferably selected from the group consisting of soybean oil, linseed oil, almond oil, castor oil, coconut oil, rapeseed oil, cottonseed oil, sunflower seed oil, groundnut oil, palm oil, palm kernel oil, sesame oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, tall oil, tung oil, cashew nutshell oil, fish oil, whale oil, and a fatty acid or a fatty acid ester derivative thereof, and combinations thereof.

In certain embodiments, the relative amounts of the reactants comprising at least one biobased oil and (meth) acrylic acid are provided in a 10:1 to a 1:100 molar ratio of biobased oil to (meth)acrylic acid, or a 10:1 to a 1:40 molar ratio, or a 10:1 to a 1:25 molar ratio, or a 1:1 to a 1:25 molar ratio, or a 3:1 to a 1:15 molar ratio, or a 1:2 to a 1:15 molar ratio of biobased oil to (meth)acrylic acid.

In certain embodiments, the method includes a combination of at least one biobased oil and (meth)acrylic acid ranging from 10% to 100% by weight of the total components present, or from 50% to 100%, or from 70% to 100%, or from 20% to 60%, or from 50% to 70%, or from 80% to 100% by weight of the total components present in the reactor.

In certain embodiments, the method includes acid catalyst comprising 0.01% to 50% by weight of the total components present, or 0.01% to 30%, or 0.01% to 20%, or 0.01% to 10%, or 1% to 50%, or 1% to 10%, by weight of the total components present in the reactor.

In certain embodiments, the method includes reacting (meth)acrylic acid with at least one biobased oil at a temperature of 40 degrees Celsius (° C.) to 150° C., or 40° C. to 110° C., or 60° C. to 150° C., or 60° C. to 110° C. These temperatures produce single pass and batch yields as well as selectivities in reasonable amounts of time.

In certain embodiments, the method includes reacting (meth)acrylic acid with at least one biobased oil at a pressure of 0.5 atmospheres (atm) (0.05 megaPascals (MPa)) to 100 atm (10.13 MPa), or 0.5 atm (0.05 MPa) to 50 atm (5.07 MPa), or 1 atm (0.10 MPa) to 20 atm (2.03 MPa), or 1 atm (0.10 MPa) to 5 atm (0.51 MPa). Reaction pressures may be controlled by a back pressure regulator placed at the outlet of the reactor unit, or other conventional methods. Typically, reaction pressures are no greater than 5 MPa, and often no greater than 1 MPa.

In certain embodiments, the method includes acrylating 5% to 99% of the unsaturations of at least one biobased oil, or 5% to 85%, or 10% to 80%, or 15% to 75%, or 20% to 50%, or 30% to 70% of the unsaturations of at least one biobased oil. The percentage of unsaturations that are acrylated may be determined, for example, using proton nuclear magnetic resonance ($^1$H NMR). One suitable method that employs $^1$H NMR to determine the average extent of acrylation is described by Zhang et al. (*Green Chem.*, 2013, vol. 15, pp. 641-645). Depending on the particular application for the (meth)acrylate functional biobased oil produced, either a lower or higher percentage of acrylation may be preferred.

In certain embodiments of methods according to the present application, reacting (meth)acrylic acid with at least one biobased oil occurs in a continuous reactor, a semi-continuous reactor, a batch reactor, or combinations thereof.

For example and without limitation, embodiments of the method employing a continuous reactor comprise charging a reactor tube with an acid catalyst material to form a packed bed, followed by a pre-mixture of (meth)acrylic acid and at least one biobased oil being fed to the packed bed reactor continuously at a predetermined temperature and pressure. For example, a liquid syringe pump would be suitable for delivering the mixture of reactants to the reactor tube. After allowing several residence times of the reactants in the reactor to reach steady state, product is collected for analysis of, for instance, a mixture of primarily (meth)acrylate functional biobased oil, (meth)acrylic acid, and biobased oil.

In one exemplary continuous process, biobased oil and (meth)acrylic acid reactants (as described herein) are mixed prior to entering or upon entering the reaction zone, defined to be the volume in the tubular reactor occupied by the heterogeneous catalyst material. The time required to perform the desired reaction can vary, primarily due to catalyst type and temperature. Reactant residence time, defined as the catalyst void volume divided by the volumetric feed rate of the reactants, may be controlled, for example, by adjusting the total reactant feed rate to the reactor. Reactant residence time is typically held constant at values of at least 1 minute, and often at least 5 minutes. Reactant residence time is typically held constant at values of no greater than 120 minutes, and often no greater than 25 minutes. Reaction temperatures may be controlled, for example, with resistively heated insulating tape or by circulating heating oil from a temperature controlled bath, or other conventional methods.

In one exemplary batch process, an acid catalyst and the at least one biobased oil and/or derivatives thereof and (meth)acrylic acid reactants (as described herein) are charged into a batch reactor, heated to a desired temperature with agitation, and reacted for a predetermined time. Acid can be removed from the product, for instance, by washing with a base such as sodium carbonate. Other suitable purification methods conventionally used in the art could alternatively be employed.

The addition of acrylic acid and/or methacrylic acid to a biobased oil according to the present disclosure is typically carried out neat, i.e., in the absence of solvent. If desired, however, solvents such as alkanes and aromatics (e.g., hexane, heptane, toluene, and xylenes) can be used.

As noted above, the oil and/or oil derivative reactant is biobased, i.e., obtained from a plant or animal source. ASTM D6866-12, "Determining the Biobased Content of Solid, Liquid, and Gaseous Samples Using Radiocarbon Analysis," provides methods for determining the source of carbon in a material using carbon dating. In particular, $^{14}$C/C and $^{13}$C/C isotopic ratios indicate if a material has a fossil (e.g., petroleum based) carbon source or a plant based carbon source. A material with a fossil carbon source contains no $^{14}$C, whereas a material with 100% $^{14}$C (after correction for 1950s nuclear testing) indicates a completely modern, biobased carbon source. In most embodiments, the (meth)acrylate functional oil comprises between 50% and 100% by weight biobased carbon, as determined using ASTM D6866-12, or between 70% and 100% by weight biobased carbon.

Exemplary Embodiments

1. A method of making a (meth)acrylate comprising reacting (meth)acrylic acid with at least one biobased oil including at least one unsaturation, the reacting occurring in the presence of an acid catalyst comprising an inorganic or organic acid having at least one oxygen atom present thereon and which possesses at least one acid functionality having an ionization constant in water which is not greater than 3.

2. The method of embodiment 1 wherein the acid catalyst comprises a heterogeneous catalyst.

3. The method of embodiment 1 wherein the acid catalyst comprises a homogeneous catalyst.

4. The method of embodiment 1 or embodiment 2 wherein the acid catalyst comprises a cation exchange resin.

5. The method of any one of embodiments 1 through 4 wherein the reacting occurs in the presence of water in an amount between 0% and 20% by weight of the total components present.

6. The method of any one of embodiments 1 through 5 wherein the reacting occurs in the presence of water in an amount between 0% and 5% by weight of the total components present.

7. The method of any one of embodiments 1 through 6 wherein the acid catalyst comprises a sulfuric acid catalyst, a sulfonic acid catalyst, or a combination thereof.

8. The method of any one of embodiments 1 through 7 wherein the acid catalyst comprises a sulfuric acid functional group, a sulfonic acid functional group, or a combination thereof, bound to a $C_1$-$C_{30}$ aliphatic group, aromatic group, or heteroalkyl group, a polymer or (co)polymer, or an inorganic group.

9. The method of any one of embodiments 1 through 8 wherein the acid catalyst is selected from the group consisting of methanesulfonic acid, p-toluenesufonic acid, fluorosulfuric acid, trifluoromethanesulfonic acid, a sulfonated styrene divinylbenzene copolymer, a fluorosulfonic acid polymer on amorphous silica support, and combinations thereof.

10. The method of any one of embodiments 1 through 9 wherein the at least one biobased oil is selected from the group consisting of soybean oil, linseed oil, almond oil, castor oil, coconut oil, rapeseed oil, cottonseed oil, sunflower seed oil, groundnut oil, palm oil, palm kernel oil, sesame oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, tall oil, tung oil, cashew nutshell oil, fish oil, whale oil, and a fatty acid or a fatty acid ester derivative thereof, and combinations thereof.

11. The method of any one of embodiments 1 through 10 wherein the (meth)acrylic acid comprises acrylic acid or methacrylic acid.

12. The method of any one of embodiments 1 through 11 wherein the (meth)acrylic acid comprises a combination of acrylic acid and methacrylic acid.

13. The method of any one of embodiments 1 through 12 wherein the at least one biobased oil and the (meth)acrylic acid are provided in a 10:1 to a 1:100 molar ratio.

14. The method of any one of embodiments 1 through 13 wherein the at least one biobased oil and the (meth)acrylic acid are provided in a 10:1 to a 1:25 molar ratio.

15. The method of any one of embodiments 1 through 14 wherein the at least one biobased oil and the (meth)acrylic acid are provided in a 3:1 to a 1:15 molar ratio.

16. The method of any one of embodiments 1 through 15 wherein the combination of the at least one biobased oil and the (meth)acrylic acid range from 10% to 100% by weight of the total components present.

17. The method of any one of embodiments 1 through 16 wherein the combination of the at least one biobased oil or derivative thereof and the (meth)acrylic acid range from 50% to 100% by weight of the total components present.

18. The method of any one of embodiments 1 through 17 wherein the combination of the at least one biobased oil and the (meth)acrylic acid range from 70% to 100% by weight of the total components present.

19. The method of any one of embodiments 1 through 18 wherein the acid catalyst comprises 0.01% to 50% by weight of the total components present.

20. The method of any one of embodiments 1 through 19 wherein the acid catalyst comprises 0.01% to 10% by weight of the total components present.

21. The method of any one of embodiments 1 through 20 wherein the reacting is performed at a temperature of 40° C. to 150° C.

22. The method of any one of embodiments 1 through 21 wherein the reacting is performed at a temperature of 60° C. to 110° C.

23. The method of any one of embodiments 1 through 22 wherein the reacting is performed at a pressure of 0.5 atm (0.05 MPa) to 100 atm (10.13 MPa).

24. The method of any one of embodiments 1 through 23 wherein the reacting is performed at a pressure of 1 atm (0.10 MPa) to 5 atm (0.51 MPa).

25. The method of any one of embodiments 1 through 24 wherein 5% to 99% of the unsaturations of the at least one biobased oil are acrylated.

26. The method of any one of embodiments 1 through 25 wherein 15% to 75% of the unsaturations of the at least one biobased oil are acrylated.

27. The method of any one of embodiments 1 through 26 wherein the reacting occurs in a continuous reactor, a semi-continuous reactor, a batch reactor, or combinations thereof.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Summary of Materials

Unless otherwise noted, all parts, percentages, ratios, etc. in the Examples and the rest of the specification are by weight. Table 1 provides a role and a source for materials used in the Examples below:

TABLE 1

| Role | Material | Source |
| --- | --- | --- |
| Reactant | soybean oil | Spectrum Chemicals, New Brunswick, NJ |
| Reactant | linseed oil | Spectrum Chemicals, New Brunswick, NJ |

TABLE 1-continued

| Role | Material | Source |
|---|---|---|
| Reactant | methyl oleate | Alfa Aesar, Ward Hill, MA |
| Reactant | acrylic acid | BASF, Florham Park, NJ |
| Reactant | methacrylic acid | Alfa Aesar, Ward Hill, MA |
| Catalyst | AMBERLYST 36D | Dow Chemical Company, Midland, MI |
| Catalyst | SAC-13 | Sigma Aldrich, St. Louis, MO |
| Catalyst | methanesulfonic acid | Sigma Aldrich, St. Louis, MO |
| Catalyst | methanesulfonic acid, anhydrous | Varsal Inc., Warminster, PA |
| Catalyst | p-toluenesulfonic acid monohydrate | Alfa Aesar, Ward Hill, MA |
| Catalyst | trifluoromethanesulfonic acid | Alfa Aesar, Ward Hill, MA |

Example 1

Direct Addition of Acrylic Acid to Soybean Oil Using Methanesulfonic Acid Catalyst To a 100 milliliter (mL) volumetric flask was added 43.45 grams (g) of soybean oil, 27.83 g of acrylic acid (containing 200 parts per million (ppm) monomethyl ether hydroquinone (MEHQ) by weight), and 3.71 g of methanesulfonic acid (≥99.5%). The mixture was heated to 90° C. with agitation and allowed to react for 3 hours. The mixture was then cooled and acids were removed by sodium carbonate base washing. The purified product was analyzed by proton NMR and it was determined that acrylic acid had been directly added to 32.4% of the unsaturations in the starting soybean oil material, which corresponds to an average of 1.38 acrylate groups per soybean oil molecule.

Example 2

Direct Addition of Acrylic Acid to Soybean Oil Using p-toluenesulfonic Acid Catalyst To a 100 mL volumetric flask was added 41.81 g of soybean oil, 26.78 g of acrylic acid (containing 200 ppm MEHQ by weight), and 6.40 g of anhydrous p-toluenesulfonic acid. Anhydrous p-toluenesulfonic acid was obtained by dissolving p-toluenesulfonic acid monohydrate in a round bottom flask with methanol and toluene, then heating at 80° C. for 4 hours at a pressure of 50 millibar (mbar) (5,000 Pa) in a rotary evaporator. The reaction mixture was heated to 80° C. with agitation and allowed to react for 1.5 hours. The mixture was then cooled and acids were removed by sodium carbonate base washing. The purified product was analyzed by proton NMR and it was determined that acrylic acid had been directly added to 22.4% of the unsaturations in the starting soybean oil material, which corresponds to an average of 0.95 acrylate groups per soybean oil molecule.

Example 3

Direct Addition of Acrylic Acid to Soybean Oil Using Methanesulfonic Acid Catalyst To a 100 mL volumetric flask was added 44.55 g of soybean oil, 28.54 g of acrylic acid (containing 200 ppm MEHQ by weight), and 7.61 g of methanesulfonic acid (≥99.5%). The mixture was heated to 80° C. with agitation and allowed to react for 3 hours. The mixture was then cooled and acids were removed by sodium carbonate base washing. The purified product was analyzed by proton NMR and it was determined that acrylic acid had been directly added to 42.6% of the unsaturations in the starting soybean oil material, which corresponds to an average of 1.82 acrylate groups per soybean oil molecule.

Example 4

Direct Addition of Acrylic Acid to Soybean Oil Using Trifluoromethanesulfonic Acid Catalyst To a 100 mL volumetric flask was added 45.48 g of soybean oil, 29.13 g of acrylic acid (containing 200 ppm MEHQ by weight), and 0.379 g of trifluoromethanesulfonic acid (≥98.0%). The mixture was heated to 70° C. with agitation and allowed to react for 1 hour. The mixture was then cooled and acids were removed by sodium carbonate base washing. The purified product was analyzed by proton NMR and it was determined that acrylic acid had been directly added to 24.5% of the unsaturations in the starting soybean oil material, which corresponds to an average of 1.04 acrylate groups per soybean oil molecule.

Example 5

Direct Addition of Methacrylic Acid to Soybean Oil Using Methanesulfonic Acid Catalyst To a 100 mL volumetric flask was added 51.09 g of soybean oil, 19.50 g of methacrylic acid (containing 200 ppm MEHQ by weight), and 4.36 g of methanesulfonic acid (≥99.5%). The mixture was heated to 80° C. with agitation and allowed to react for 3 hours. The mixture was then cooled and acids were removed by sodium carbonate base washing. The purified product was analyzed by proton NMR and it was determined that methacrylic acid had been directly added to 14.8% of the unsaturations in the starting soybean oil material, which corresponds to an average of 0.95 methacrylate groups per soybean oil molecule.

Example 6

Direct Addition of Acrylic Acid to Linseed Oil Using Methanesulfonic Acid Catalyst To a 100 mL volumetric flask was added 44.55 g of linseed oil, 28.54 g of acrylic acid (containing 200 ppm MEHQ by weight), and 7.61 g of methanesulfonic acid (anhydrous). The mixture was heated to 80° C. with agitation and allowed to react for 2 hours. The mixture was then cooled and acids were removed by sodium carbonate base washing. The purified product was analyzed by proton NMR and it was determined that acrylic acid had been directly added to 46.6% of the unsaturations in the starting linseed oil material, which corresponds to an average of 1.88 acrylate groups per linseed oil molecule.

Example 7

Direct Addition of Acrylic Acid to Methyl Oleate Using Methanesulfonic Acid Catalyst To a 100 mL volumetric flask was added 48.35 g of methyl oleate, 23.50 g of acrylic acid (containing 200 ppm MEHQ by weight), and 3.13 g of methanesulfonic acid (≥99.5%). The mixture was heated to 80° C. with agitation and allowed to react for 3 hours. The mixture was then cooled and acids were removed by sodium carbonate base washing. The purified product was analyzed by proton NMR and it was determined that acrylic acid had been directly added to 32.2% of the unsaturations in the starting methyl oleate material.

Example 8

Direct Addition of Acrylic Acid to Soybean Oil Using AMBERLYST 36D Heterogeneous Acid Catalyst To a 100 mL volumetric flask was added 39.62 g of soybean oil, 25.37 g of acrylic acid (containing 200 ppm MEHQ by weight), and 10 g of AMBERLYST 36D (a sulfonated styrene divinylbenzene copolymer) heterogeneous acid catalyst material. The mixture was heated to 80° C. with agitation and allowed to react for 3 hours. The mixture was then cooled and acids were removed by sodium carbonate base washing. The purified product was analyzed by proton NMR and it was determined that acrylic acid had been directly added to 21.6% of the unsaturations in the starting soybean oil material, which corresponds to an average of 0.92 acrylate groups per soybean oil molecule.

Example 9

Direct Addition of Acrylic Acid to Soybean Oil Using SAC-13 Heterogeneous Acid Catalyst To a 100 mL volumetric flask was added 39.62 g of soybean oil, 25.37 g of acrylic acid (containing 200 ppm MEHQ by weight), and 5 g of oven dried (110° C. for 6 hours) SAC-13 (fluorosulfonic acid nafion polymer on amorphous silica support) heterogeneous acid catalyst material. The mixture was heated to 80° C. with agitation and allowed to react for 2 hours. The mixture was then cooled and acids were removed by sodium carbonate base washing. The purified product was analyzed by proton NMR and it was determined that acrylic acid had been directly added to 9.9% of the unsaturations in the starting soybean oil material, which corresponds to an average of 0.42 acrylate groups per soybean oil molecule.

Example 10

Direct Addition of Acrylic Acid to Soybean Oil Using a Packed Bed Reactor

A 0.493 inch (1.252 centimeter (cm)) inner diameter (I.D.) by 12 inch (30.48 cm) length stainless steel reactor tube was charged with 20 g of AMBERLYST 36D catalyst material (a sulfonated styrene divinylbenzene copolymer). A mixture containing 536 g of soybean oil and 343 g of acrylic acid (containing 200 ppm MEHQ by weight) was fed continuously to the reactor at 1 mL min$^{-1}$ total flow rate (0.00063 mol min$^{-1}$ or 0.57008 g min$^{-1}$ of soybean oil, 0.00507 mol min$^{-1}$ or 0.36516 g min$^{-1}$ of acrylic acid) corresponding to a reactant residence time in the catalyst bed of approximately 25 minutes. Reactor temperature was held constant at 80° C. After allowing three residence times to reach steady state, product was collected for analysis by proton NMR. It was determined that acrylic acid had been directly added to 7.37% of the unsaturations in the starting soybean oil material, which corresponds to an average of 0.31 acrylate groups per soybean oil molecule.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A method comprising reacting (meth)acrylic acid with a biobased oil comprising at least one unsaturation; the reacting occurring in the presence of an acid catalyst comprising an inorganic or organic acid having at least one oxygen atom present thereon and which possesses at least one acid functionality having an ionization constant in water which is not greater than 3.

2. The method of claim 1 wherein the acid catalyst comprises a heterogeneous catalyst.

3. The method of claim 1 wherein the acid catalyst comprises a homogeneous catalyst.

4. The method of claim 2 wherein the acid catalyst comprises a cation exchange resin.

5. The method of claim 1 wherein the acid catalyst comprises a sulfuric acid catalyst, a sulfonic acid catalyst, or a combination thereof.

6. The method of claim 1 wherein the reacting occurs in the presence of water in an amount between 0% and 5% by weight of the total components present.

7. The method of claim 1 wherein the acid catalyst comprises a sulfuric acid functional group, a sulfonic acid functional group, or a combination thereof, bound to a $C_1$-$C_{30}$ aliphatic group, aromatic group, or heteroalkyl group, a polymer or (co)polymer, or an inorganic group.

8. The method of claim 1 wherein the acid catalyst is selected from the group consisting of methanesulfonic acid, p-toluenesufonic acid, fluorosulfuric acid, trifluoromethanesulfonic acid, a sulfonated styrene divinylbenzene copolymer, a fluorosulfonic acid polymer on amorphous silica support, and mixtures thereof.

9. The method of claim 1 wherein the at least one biobased oil is selected from the group consisting of soybean oil, linseed oil, almond oil, castor oil, coconut oil, rapeseed oil, cottonseed oil, sunflower seed oil, groundnut oil, palm oil, palm kernel oil, sesame oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, tall oil, tung oil, cashew nutshell oil, fish oil, whale oil, and a fatty acid or a fatty acid ester derivative thereof.

10. The method of claim 1 wherein the (meth)acrylic acid comprises acrylic acid or methacrylic acid.

11. The method of claim 1 wherein the biobased oil and the (meth)acrylic acid are provided in a 10:1 to a 1:100 molar ratio.

12. The method of claim 11 wherein the biobased oil and the (meth)acrylic acid are provided in a 10:1 to a 1:25 molar ratio.

13. The method of claim 1 wherein the combination of the biobased oil and the (meth)acrylic acid range from 10% to 100% by weight of the total components present.

14. The method of claim 13 wherein the combination of the biobased oil and the (meth)acrylic acid range from 50% to 100% by weight of the total components present.

15. The method of claim 1 wherein the acid catalyst comprises 0.01% to 50% by weight of the total components present.

16. The method of claim 1 wherein the reacting is performed at a temperature of 40° C. to 150° C.

17. The method of claim 16 wherein the reacting is performed at a temperature of 60° C. to 110° C.

18. The method of claim 1 wherein the reacting is performed at a pressure of 0.5 atm (0.05 MPa) to 100 atm (10.13 MPa).

19. The method of claim 1 wherein 15% to 75% of the unsaturations of the biobased oil are acrylated.

20. The method of claim 1 wherein the reacting occurs in a continuous reactor, a semi-continuous reactor, a batch reactor, or combinations thereof.

* * * * *

UNITED STATES PATENT AND TRADEMARK OFFICE
CERTIFICATE OF CORRECTION

PATENT NO. : 9,533,935 B2
APPLICATION NO. : 14/778644
DATED : January 3, 2017
INVENTOR(S) : Joshua Colby It is certified that error appears in the above-identified patent and that said Letters Patent is hereby corrected as shown below:

On the Title Page

Column 2, Line 1, under "Other Publications", delete "polymerizatin" and insert -- polymerization --, therefor.

Column 2, Line 4, under "Other Publications", delete "Preparatinof" and insert -- Preparation of --, therefor.

Column 2, Line 4, under "Other Publications", delete "urethanated" and insert -- urethanized --, therefor.

Column 2, Line 15, under "Other Publications", delete "aliphaticacid" and insert -- aliphatic acid --, therefor.

In the Specification

Column 5,
Line 14, delete "polynuclear aromatic hydrocarbon group." and insert the same on Column 5, Line 13, as a continuation of the same paragraph.

Column 6,
Line 58, delete "p-toluenesufonic" and insert -- p-toluenesulfonic --, therefor.

Column 11,
Line 32, delete "p-toluenesufonic" and insert -- p-toluenesulfonic --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,533,935 B2

In the Claims

Column 16,
Line 39, in Claim 8, delete "p-toluenesufonic" and insert -- p-toluenesulfonic --, therefor.